(12) United States Patent
Ross

(10) Patent No.: US 7,372,044 B2
(45) Date of Patent: May 13, 2008

(54) UV STERILIZATION OF USER INTERFACE FOMITES

(76) Inventor: Andrew Ross, P.O. Box 9575, Rancho Santa Fe, CA (US) 92067

( * ) Notice: Subject to any disclaimer, the term of this patent is extended or adjusted under 35 U.S.C. 154(b) by 169 days.

(21) Appl. No.: 11/436,288

(22) Filed: May 17, 2006

(65) Prior Publication Data

US 2008/0067418 A1    Mar. 20, 2008

(51) Int. Cl.
*A61L 2/10* (2006.01)
*A61L 9/20* (2006.01)

(52) U.S. Cl. ............... 250/455.11; 250/504 R; 250/461.1; 250/365; 422/24; 422/121

(58) Field of Classification Search ............ None
See application file for complete search history.

(56) References Cited

U.S. PATENT DOCUMENTS

| | | |
|---|---|---|
| 2,822,476 A | 2/1958 | Osgood |
| 4,464,336 A | 8/1984 | Hiramoto |
| 4,469,835 A | 9/1984 | Laurin |
| 4,806,770 A | 2/1989 | Hylton et al. |
| 4,868,397 A | 9/1989 | Tittel |
| 4,877,964 A | 10/1989 | Tanaka et al. |
| 4,950,902 A | 8/1990 | Ritter |
| 4,973,847 A | 11/1990 | Lackey et al. |
| 5,023,460 A | 6/1991 | Foster, Jr. et al. |
| 5,126,572 A | 6/1992 | Chu |
| 5,144,146 A | 9/1992 | Wekhof |
| 5,671,314 A | 9/1997 | Gregory et al. |
| 5,688,475 A | 11/1997 | Duthie, Jr. |
| 6,087,781 A | 7/2000 | Leppelmeier |
| 6,171,548 B1 * | 1/2001 | Rose et al. ............ 422/20 |
| 6,461,568 B1 * | 10/2002 | Eckhardt ............ 422/24 |
| 6,576,188 B1 * | 6/2003 | Rose et al. ............ 422/20 |
| 6,646,270 B2 | 11/2003 | Cunningham |
| 2007/0023710 A1 * | 2/2007 | Tom et al. ............ 250/504 R |

FOREIGN PATENT DOCUMENTS

| | | |
|---|---|---|
| EP | 0 925 794 A2 | 6/1999 |
| FR | 2 753 905 | 4/1998 |
| GB | 1195209 | 6/1970 |
| JP | 09000608 | 1/1997 |
| WO | WO 03/094691 A1 | 11/2003 |

OTHER PUBLICATIONS

UVSolutions, retrieved from the internet at http://www.uvs-ultraclean.com/index.htm.

* cited by examiner

*Primary Examiner*—Nikita Wells
(74) *Attorney, Agent, or Firm*—Fish & Richardson P.C.

(57) ABSTRACT

Techniques for sterilizing a fomite are disclosed. A UV sterilization apparatus includes a housing for enveloping a fomite inside the housing. The housing is composed of a material that prevents transmission of electromagnetic radiation in the ultraviolet range. Attached to the housing is a closure element, and the closure element is also composed of a material that prevents transmission of electromagnetic radiation in the UV range but allows transmission of electromagnetic radiation in the visual range. An ultraviolet light source is attached to an internal surface of the housing or an internal surface of the closure element, and the light source sterilizes the fomite enclosed inside the housing by transmitting ultraviolet electromagnetic radiation towards the fomite.

34 Claims, 7 Drawing Sheets

UV STERILIZATION OF USER INTERFACE FOMITES

TECHNICAL FIELD

The present disclosure relates to sterilization techniques using ultraviolet (UV) electromagnetic radiation. For example, UV sterilization techniques can be applied to sterilize user interface fomites such as a computer keyboard and a telephone.

BACKGROUND

Fomites are inanimate objects that can carry infectious pathogenic microorganisms such as bacteria, spores, viruses, and fungi. Depending on the nature, use and location of the fomites, certain fomites are more susceptible to be carriers for disease causing microorganisms. For example, a hospital is an environment with multiple sources of disease carrying infectious pathogenic microorganisms. The possible cross contaminations include patient to staff, staff to staff, and staff to patient. While some fomites in a hospital can be easily sterilized, sterilizing electronic fomites such as a keyboard or a telephone can be problematic. A keyboard or a telephone cannot be autoclaved due to the sensitive electrical elements housed inside the plastic outer shell. While an alcohol wash can be applied, extreme care is required to avoid short circuiting the electrical elements with the alcohol liquid and thus rendering the fomites permanently damaged.

SUMMARY

Techniques for sterilizing user interface fomites using UV electromagnetic radiation are disclosed.

In an implementation, a system for sterilizing a fomite can include a housing able to envelop a fomite inside the housing. The housing is composed of a material or a combination of materials that prevents transmission of electromagnetic radiation in the ultraviolet range. A closure element is attached to the housing, and the closure element is also composed of a material or a combination of materials that prevents transmission of electromagnetic radiation in the ultraviolet range but allows visual light to pass through the closure element. The system also includes an ultraviolet (UV) light source located inside the housing. The UV light source is capable of sterilizing the fomite enclosed inside the housing by directing ultraviolet electromagnetic radiation towards the fomite.

Implementations can include one or more of the following features. For example, the closure element can be implemented to include an automated closure element, a sliding closure element, a rotating closure element, an integrally formed closure element, or a closure elements with separate pieces. The closure element can be also be a door. The fomite can be permanently attached to the housing or detachably attached to the housing. The housing can envelop a computer keyboard and a computer mouse inside the housing. Alternatively, the housing can envelop a telephone that includes a receiver and a control module. For the housing enveloping the telephone, a second ultraviolet light source can be included to sterilize the receiver by directing ultraviolet electromagnetic radiation towards the underside of the receiver. The system can further include an interface module. The interface module can include a power outlet for plugging-in power cords and a computer input/output interface module for physically connecting to a plurality of computer peripheral devices permanently or detachably connected to the housing. The computer input/output interface can include at least one of a universal serial bus port, a FireWire port, a peripheral component interconnect port, a serial interface port, and a parallel interface port. The interface module can also include a telephone jack.

Implementations can further include one or more of the following features. For example, the housing can include an automatic switch linked to the closure element. The automatic switch can be designed to turn-on the ultraviolet light source for a predetermined period of time when the closure element is closed and to automatically turn-off the ultraviolet light source when the closure element is open. Alternatively, a programmable timing module can be included and connected to the automatic switch and the closure element. The programmable timing module can be programmed to periodically turn-on and turn-off the ultraviolet light for a predetermined period of time. In addition, a motor can be connected to the closure element to automatically open and close the closure element. The motor can be operated by having an automatic control module sending a signal to the motor to automatically open and close the closure element. The automatic module can be a motion detector.

The details of one or more embodiments are set forth in the accompanying drawings and the description below. Other features and advantages of the techniques will be apparent from the description and drawings, and from the claims.

DESCRIPTION OF DRAWINGS

Like reference symbols in the various drawings indicate like elements.

DETAILED DESCRIPTION

UV System Design for Sterilizing Fomites

Figure 1A:
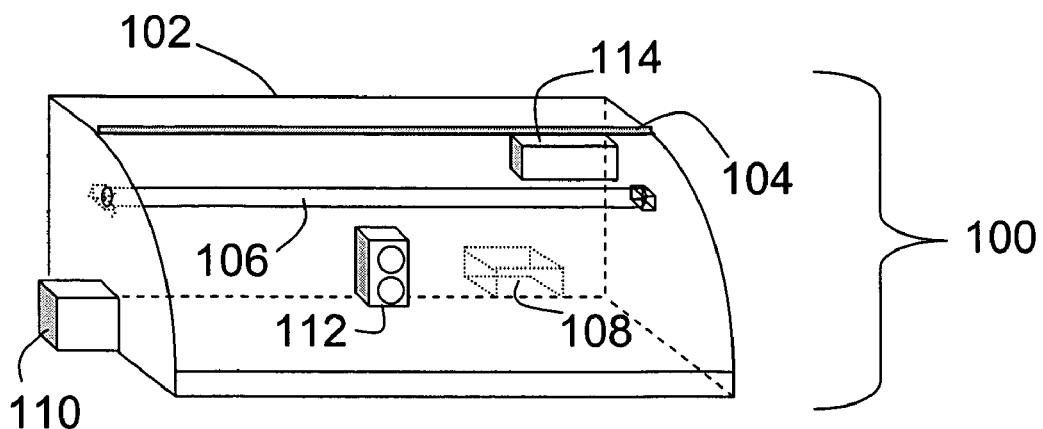
FIG. 1A is a front view of a UV system for sterilizing a fomite with a closure element open.
Figure 1B:
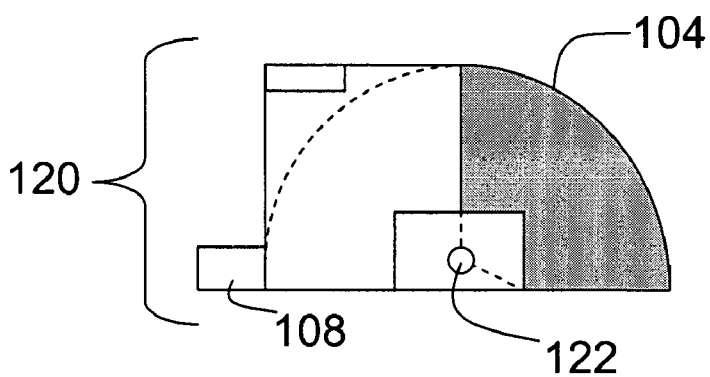
FIG. 1B is a side view of a UV system for sterilizing a fomite.
Figure 1C:
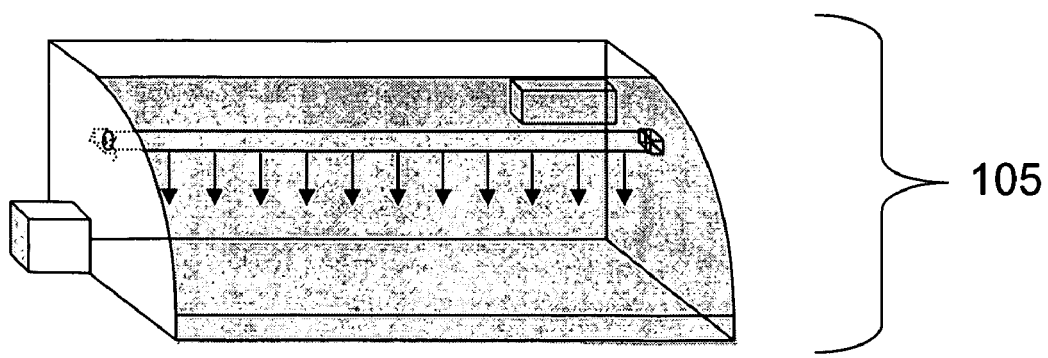
FIG. 1C is a front view of a UV system for sterilizing a fomite with the closure element closed.

FIGS. 1A-C describe a system for sterilizing a fomite using ultraviolet electromagnetic radiation (the "UV system"). The UV system comprises a housing 102, a closure element 104, an ultraviolet (UV) light source 106, a motor 108, and an automatic controller 110. The UV system can optionally include an electrical interface 112 and a programmable timer 114. FIG. 1A is a front view 100 of the UV system with the closure element 104 at an open position. FIG. 1B is a side view 120 of the UV system showing the axis of rotation 122 for the closure element 104 when toggling between an open position and a closed position. FIG. 1C is another front view 105 of the UV system with the closure element 104 at the closed position.

The housing 102 is composed of a material or a combination of materials designed to prevent transmission of electromagnetic radiation in the UV range. The typical UV radiation has a wavelength shorter than that of the visible light, but longer than that of soft X-rays. UV radiation can be subdivided into near UV (380-200 nm wavelength), far or vacuum UV (200-10 nm; FUV or VUV), and extreme UV (1-31 nm; EUV or XUV). When considering the effect of UV radiation on human health and the environment, the range of UV wavelength can also be subdivided into Long Wave or "blacklight" (380-315 nm; UVA); Medium Wave (315-280 nm; UVB); and Short Wave (<280 nm; UVC).

The material for the housing 102 can also be designed to optionally allow transmission of visible light in order to allow a user to see inside the housing. Movably attached to the housing 102 is the closure element 104, which is also composed of a material or a combination of materials designed to prevent transmission of electromagnetic radiation in the UV range. Preferably, the closure element 104 also allows transmission of visible light to allow a user to see through the door and inside the housing. Importance of the housing 102 and the door 104 to prevent transmission of UV electromagnetic radiation will be described below with respect to the sterilization process.

The UV system also includes an UV light source 106 located inside of the housing 102. FIGS. 1A and 1C illustrates an implementation with the UV light source 106 attached to the internal side wall surfaces. In some implementations, the UV light source 106 can be attached to any other suitable internal surfaces of the housing 102 or an internal surface of the closure element 104. The UV light source 104 is configured to optimize sterilization of the internal environment of the housing 102. For example, commercially available low pressure mercury-vapor UV lamps emit about 86% of their light at 254 nm, which coincides with one of two peaks of the germicidal effectiveness curve, 265 nm and 185 nm. The germicidal effectiveness curve describes the effectiveness for UV absorption by DNA. UV light at these wavelengths causes adjacent thymine molecules on DNA to dimerize, a combination of two monomers or subunits, and create a defect in the DNA. Substantial accumulation of such defects inserted into a microorganism's DNA inhibits replication and renders the microorganism harmless.

The UV system is configured to envelop one or more fomites inside the housing 102. The electronic fomites can be user interface fomites such as a computer keyboard, a computer mouse, and a telephone. Other suitable fomites susceptible to repeated public usage can also be housed in the UV system. The housing 102 is implemented to permanently envelop one or more fomites. But in some implementation, the housing 102 is implemented to detachably envelop one or more fomites. Yet in other implementations, the housing 102 is implemented to envelop or hold one or more fomites inside the housing 102 without permanently or detachably attaching to the housing 102.

Figure 2A:
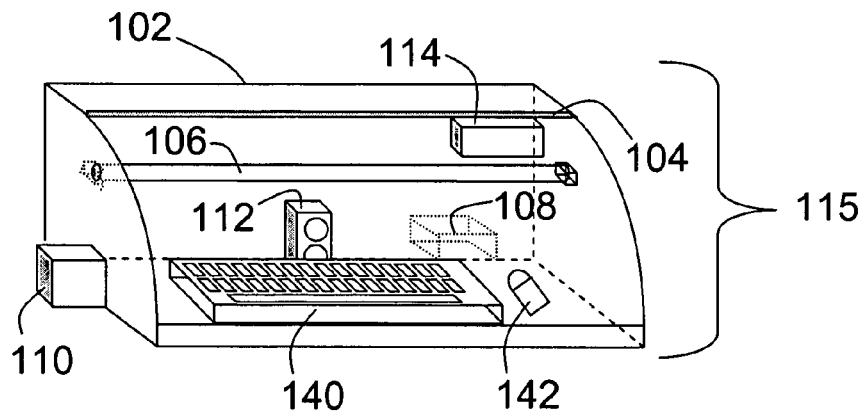
FIG. 2A is a front view of a UV system for sterilizing electronic fomites.
Figure 2B:
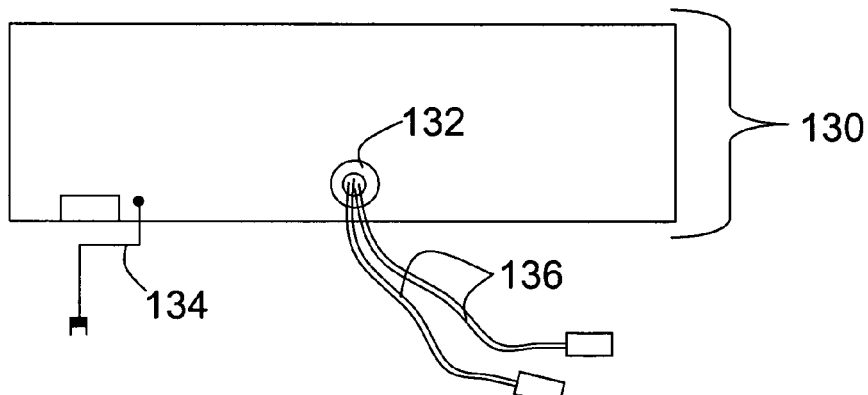
FIG. 2B is a back view of a UV system for sterilizing electronic fomites.
Figure 2C:
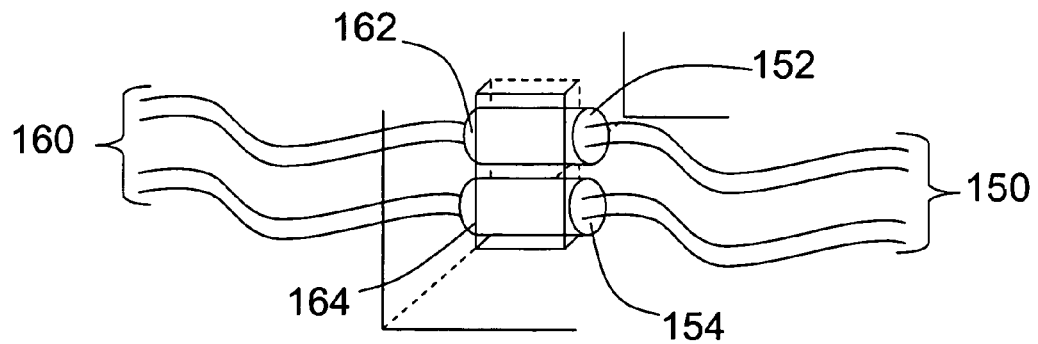
FIG. 2C is a detailed view of electronic connections in a UV system for sterilizing electronic fomites.

FIG. 2A is a front view 115 of an implementation for housing a computer keyboard 140 and a mouse 142. If the computer keyboard 140 and the mouse 142 are wired devices, the UV system can be implemented to include an interface 112 for allowing computer cables/wires 136 attached to the computer keyboard 140 and the mouse 142 to pass through one or more surfaces of the housing 102. FIG. 2B is an external back surface view 125 of the UV system illustrating a portal 132 created by the interface 112 for allowing the computer cables/wires 136 to pass through the back surface of the housing 102. The portal 132 is designed to prevent transmission of UV electromagnetic radiation through the portal 132. Preferably, the portal includes a flexible rubber-like material for creating air tight seal around the computer cables/wires 136 and preventing transmission of electromagnetic radiation in the UV range.

In some implementations, other suitable materials or designs can be implemented to prevent transmission of UV electromagnetic radiation through the portal 132.

The computer cables/wires 136 can include an Universal Serial Bus interface (USB) cable, an FireWire cable, and other serial or parallel interface cables. The back surface view 125 also illustrates a power cord 134 for providing electrical power required to operate the UV light source 106.

In some implementations, the interface 112 is implemented to generate a physical port or bridge between an external computing device and the computer keyboard 140 and the mouse 142. Computer cables/wires 150 connected to the computer keyboard 140 and the mouse 142 are plugged into internal ports 152, 154 located inside of the housing 102. A second set of computer cables/wires 160 are plugged into external ports 162, 164 at one end of the cables/wires and plugged into suitable computer input/output (I/O) ports of an external computing device (e.g., a desktop computer) at the other end. Appropriate female and male connectors are implemented to ensure proper connections at all ports. For example, if the computer cables/wires 150, 160 are USB cables, the internal ports 152, 154; external ports 162, 164; and computer I/O ports are appropriate USB ports.

In some implementations, the computer keyboard 140 and the mouse 142 are wireless devices and the UV system does not require implementing the interface 112.

For implementations where the UV system houses and sterilizes the computer keyboard 140 and the mouse 142, the UV system can be implemented to detachably affix the computer keyboard 140 and the mouse 142 inside of the housing 102. Such implementations allow a user to replace a preexisting keyboard or mouse with a different keyboard or mouse when the keyboard or the mouse is defective or to simply upgrade the keyboard or the mouse to take advantage of different or new features.

In some implementations, the UV system comprising the housing 102, the closure element 104, and the UV light source 106 is manufactured permanently attached to a computer keyboard 140 and/or a mouse 142. Manufacturing the keyboard 140 with a built in sterilization system can prevent undesired removal of the keyboard 140 from the sterilization system and ensure that the keyboard 140 will be maintained in an optimally sterilized environment.

Closure Element Operation

In the preferred implementation, operation of the sterilization system is automated and "touch-less" to prevent contamination of the exterior surfaces of the system from unnecessary contact by a user. However, in some implementations, the system can be implemented to provide for a manually operated closure element 104.

Figure 3:
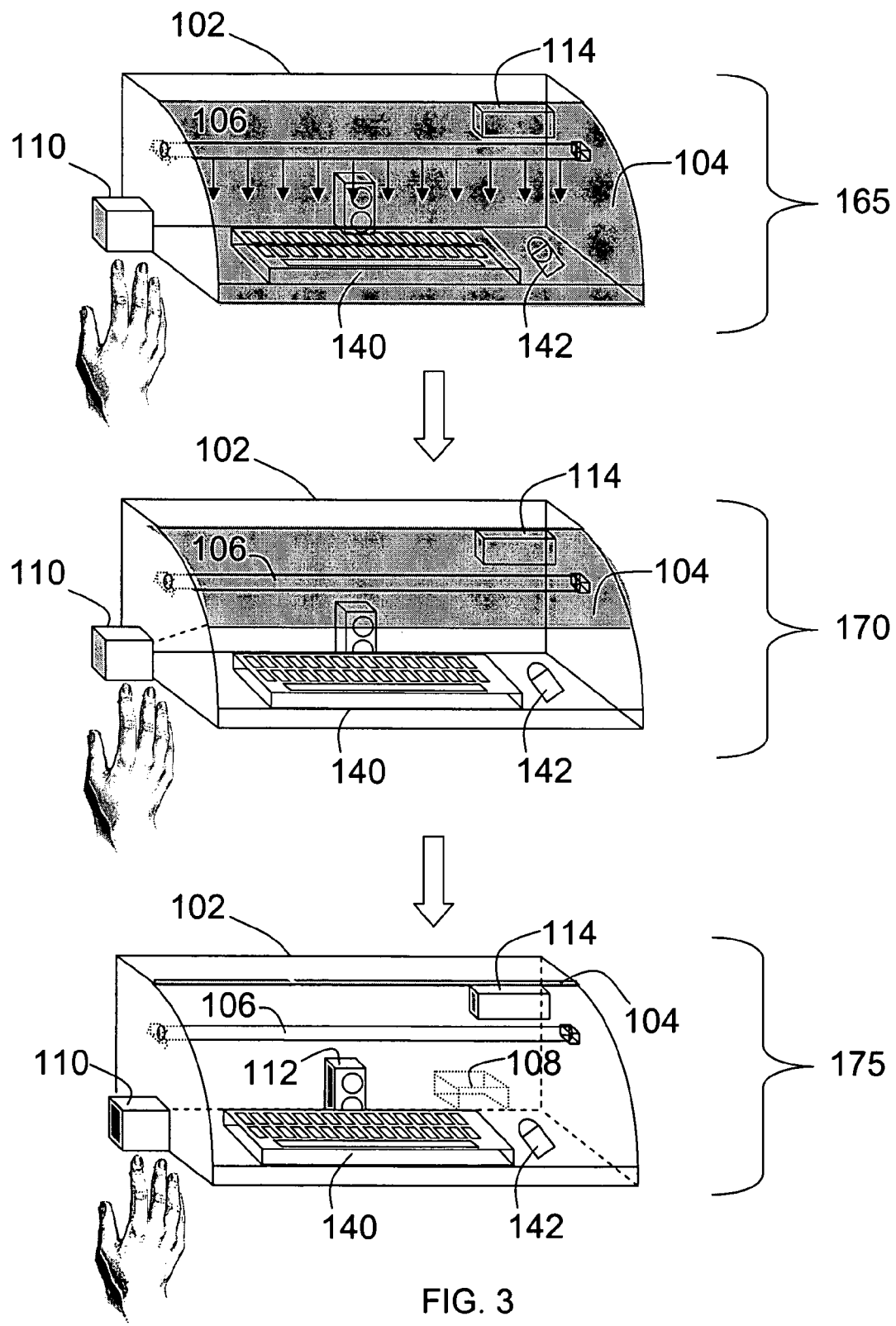
FIG. 3 is a front view of a UV system for sterilizing electronic fomites illustrating the closure element in operation.

FIG. 3 describes an operation of the sterilization system in one aspect of the techniques for sterilizing fomites. A user approaches the sterilization system having a computer keyboard 140 and a mouse 142 located inside the housing 102.

The closure element 104 is at a closed state 165. Inside the housing 102, the UV light source 106 is energized and radiates electromagnetic radiation in the UV range, and the UV electromagnetic radiation is directed toward the keyboard 140 and the mouse 142. The UV light source 106 radiates electromagnetic radiation having a wavelength of 254 nm. In some implementations, the UV light source 106 can have other suitable wavelength substantially close to 265 nm or 185 nm.

To operate the closure element 104, the user positions his hand near the automatic controller 110 to activate the closure element 104. The closure element 104 automatically transitions from the closed state 165 to an open state 175. In the preferred implementation, the automatic controller 110 is a motion sensor that detects the movement of the user's hand to activate the closure element 104 to transition from the closed state 165 to the open state 175. For example, the automatic controller 110 can be a sensor bay, and when the light beam in the sensor bay is interrupted, the motor 108 is triggered to open the closure element 104. In some implementations, the motion sensor can include a microwave motion sensor, an infrared motion sensor, and an infrared combination motion and presence sensor. In some implementations, the automatic controller 110 includes other suitable touch-less switches or sensors. When the motion sensor is engaged, a signal is sent to the motor 108 to activate the motor 108. The closure element 104 is communicatively and physically linked to the motor 108. Activation of the motor 108 enables the physical movements of the closure element 104 to transition from the open state 165 to the closed state 175.

While FIGS. 1-4 show the automatic controller 110 located on the left side of the UV system, in some implementations, the automatic controller 110 is implemented to be placed on the right side of the housing 102 or other suitable locations. Similarly, the location of the motor 108 can be moved to other suitable locations depending on the desired functionalities or manufacturing advantages gained.

The UV light source 106 is communicatively linked to the closure element 104. When the closure element 104 is activated to transition from the closed state 165 to the open state 175, the physical movement of the closure element 104 initiates shutoff procedure for the UV light source 106. In the preferred implementation, the UV light source 106 shuts off or deactivates just before the initial movement of the closure element 104 transitioning from the closed state 165 to the open state 175. In some implementation, the UV light source 106 is designed to turn off, synchronized with the activation of the automatic controller 110. In some implementations, other suitable turnoff procedure can be implemented to ensure the UV light source 106 is turned off before the physical movement of the closure element 104. Proper shutoff of the UV light source is important to prevent transmission of UV electromagnetic radiation through an opening created by the closure element 104. Prolonged exposure to UV electromagnetic radiation can create undesired defects in the DNA of the user and resulting in a dangerous medical condition. To illustrate the physical movement of the closure element 104, FIG. 3, illustrates the closure element 104 half open 170 and on its way to being fully open 175.

Figure 4:
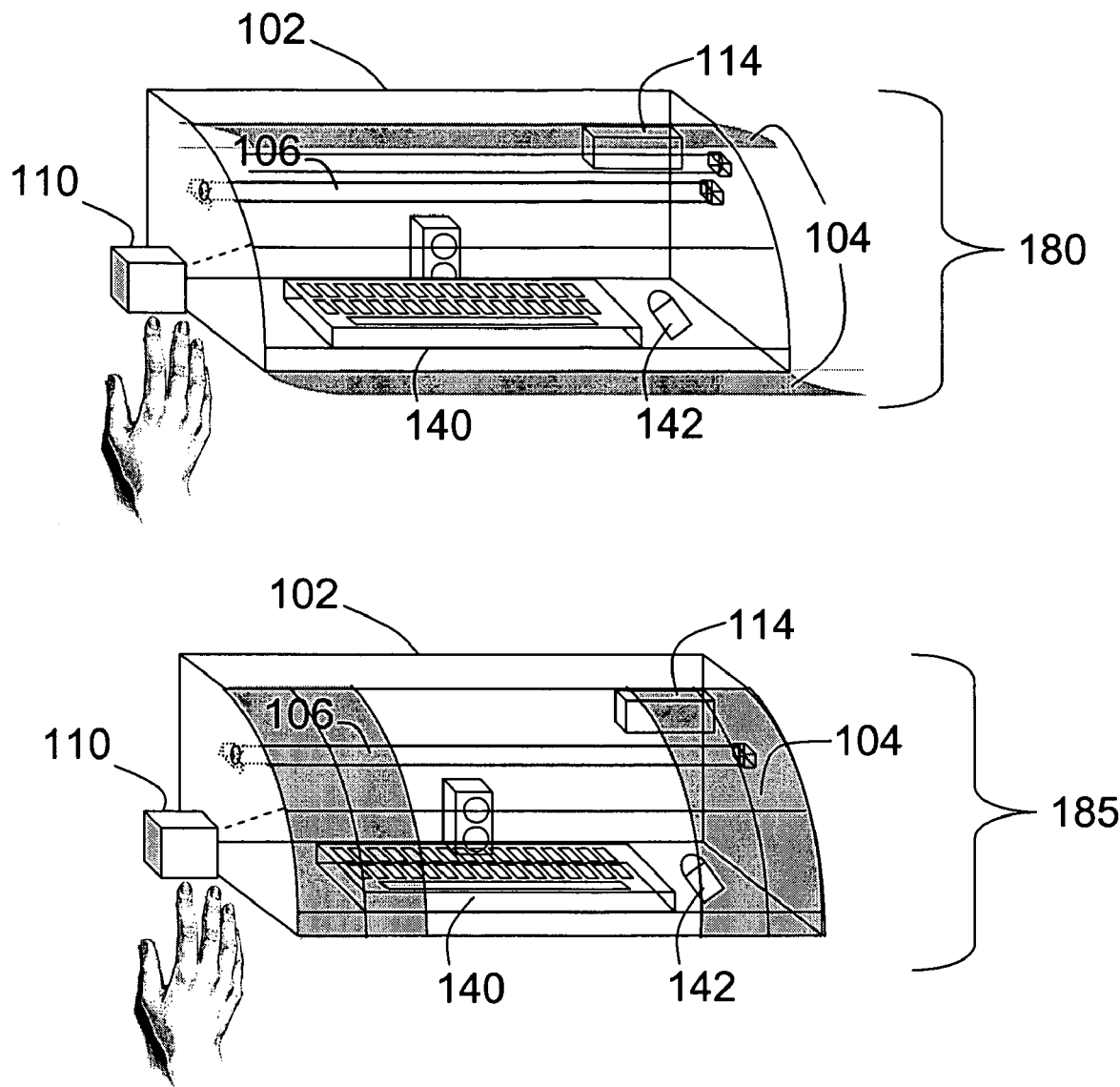
FIG. 4 is a front view of a UV system for sterilizing electronic fomites with optional closure elements.

In some implementations, the closure element 104 is implemented to open and close in other suitable manners. FIG. 4 illustrate alternate implementations for designing and operating the closure element 104. For example, the closure element 104 can be implemented as two segments that slide, rotate, or flip open vertically as illustrated at 180. Alternatively, the closure element 104 can be implemented as multiple segments that slide open horizontally as demonstrated at 185. The closure element 104 can also be an integrally formed piece. Further, the closure element 104 can be implemented as a door, a lid, a cover, or other suitably movable element. Other variations in the design and operation of the closure element 104 are within the scope of this disclosure.

Sterilization Process

Figure 5:
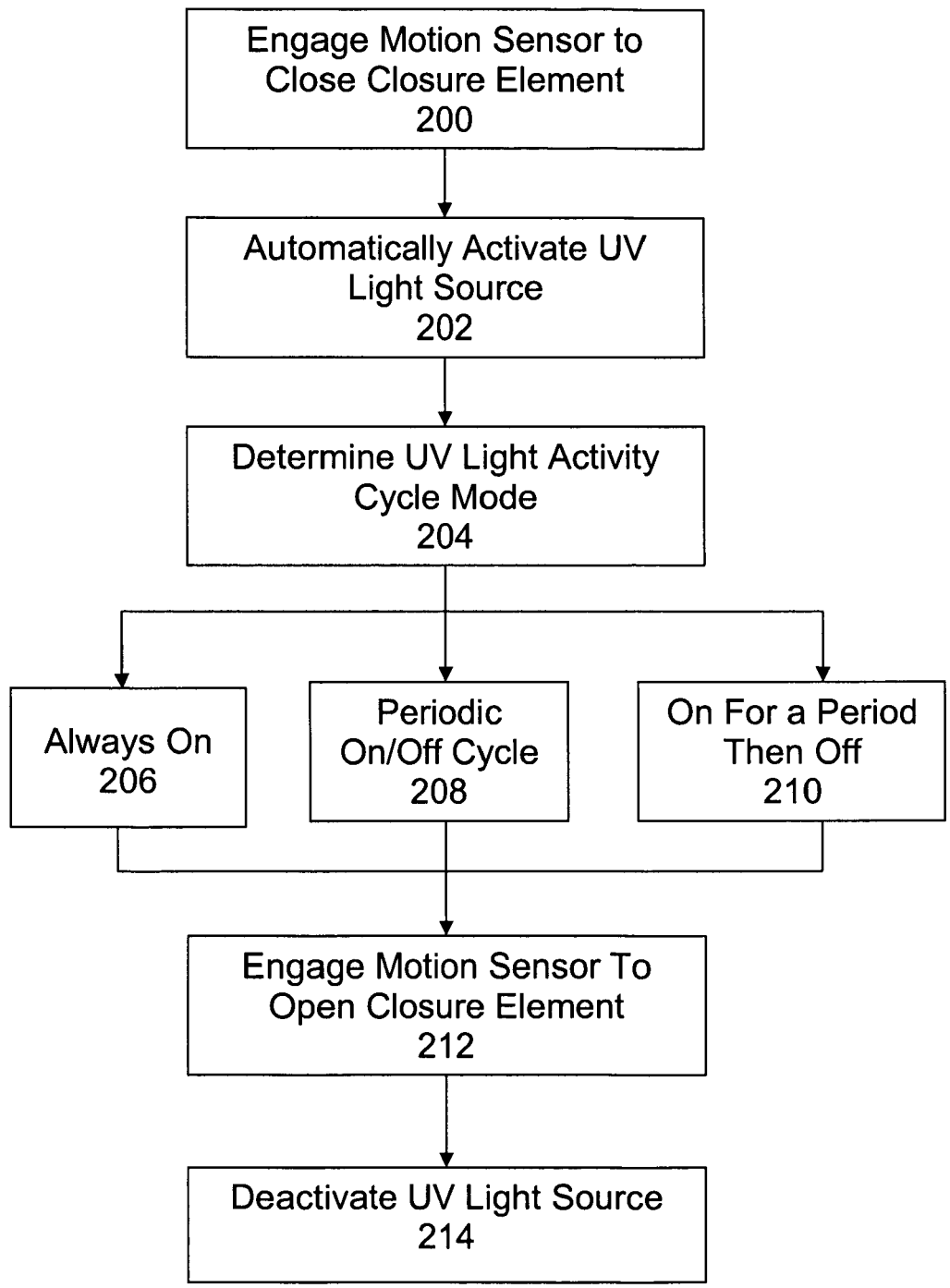
FIG. 5 is a flow diagram of a process for sterilizing electronic fomites.

When the closure element 104 is closed and the UV light source 106 is activated, the electromagnetic radiation is directed towards the fomites enclosed or enveloped in the housing 102 to effectively sterilize the entire internal surfaces of the housing 102 including the fomites as shown in FIG. 5. After the user has finished using the computer keyboard 140, the user waves his hand near the automatic controller 110 to engage the motion sensor and initiates the enclosure element 104 closing process at 200. The motion sensor sends a signal to the motor 108 to close the closure element 104. Once the closure element 104 is closed, the UV light source is automatically engaged at 202, and electromagnetic radiation in the UV range is dispersed throughout the internal surfaces of the housing 102 and the electronic fomites enclosed within, such as the computer keyboard 140.

The housing 102 and the closure element 104 are composed of a material or a combination of materials that prevent transmission of electromagnetic radiation in the UV range. By preventing transmission of electromagnetic radiation in the UV range, the UV electromagnetic radiation is contained within the housing to effectively sterilize the fomite and all internal surfaces of the housing. Further, preventing transmission of UV electromagnetic radiation protects the user from absorbing a harmful dose of UV electromagnetic radiation.

To sterilize the internal environment of the housing 102, at least three sets of active or "on" modes for the UV light source 106 can be determined and identified at 204. The UV light source 106 can be programmed to stay on ("Always On" at 206) until the closure element 104 is engaged to open by a user. Alternatively, the UV light source 106 can be programmed to periodically turn on and off for a predetermined time period at 208. Also, the UV light source 106 can be programmed to stay on for a predetermined time period and then automatically shut off at 210. In the preferred implementation, the programmable timer 114 (FIG. 1A) is implemented to allow a user to select from the three modes described above and to program the predetermined time periods for the modes. The programmable timer 114 is preferably implemented to locate inside of the housing 102 to keep the programmable timer 114 sterilized. However, in some implementations, the programmable timer 114 can be located on an outer surface of the housing 102. The programmable timer 114 can be a simple switch or a user interface with either physical or graphical representations of buttons, selectors, menus, and other suitable selection items.

In some implementations, the UV system is implemented with a predetermined and preset UV light source mode at the time of manufacture for simplicity of operation by a user requiring little or no special skills. In such implementations, the programmable timer 114 is not needed.

If the UV light source 106 is active (turned on) when the user engages the motion sensor to open the closure element 104 at 212, the activation of the motion sensor and the closure element 104 immediately shuts off the UV light source 106 at 214 to prevent harmful exposure of the user to the UV electromagnetic radiation. Shutting off of the UV light source 106 initiated by the opening of the closure element 104 resets all timing for the UV light source 106 if applicable.

While FIGS. 1-4 discloses a UV system implemented to envelop a computer keyboard 140 and a mouse 142, the UV system can be implemented to envelop other suitable fomites including user interface fomites such as a telephone.

UV System for Sterilizing a Telephone

The techniques can be implemented to sterilize other suitable electronic fomites susceptible to repeated public or shared use. For example, the techniques can be implemented to sterilize a telephone located at a hospital, daycare, hospice, and other public locations where reducing cross contaminations is desirable.

Figure 6A:
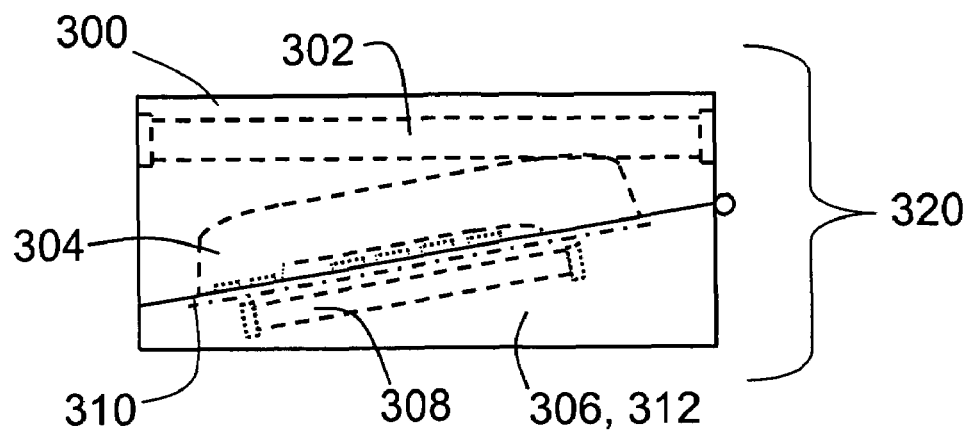
FIG. 6A illustrates right side views of a UV system for sterilizing a telephone.
Figure 6A:
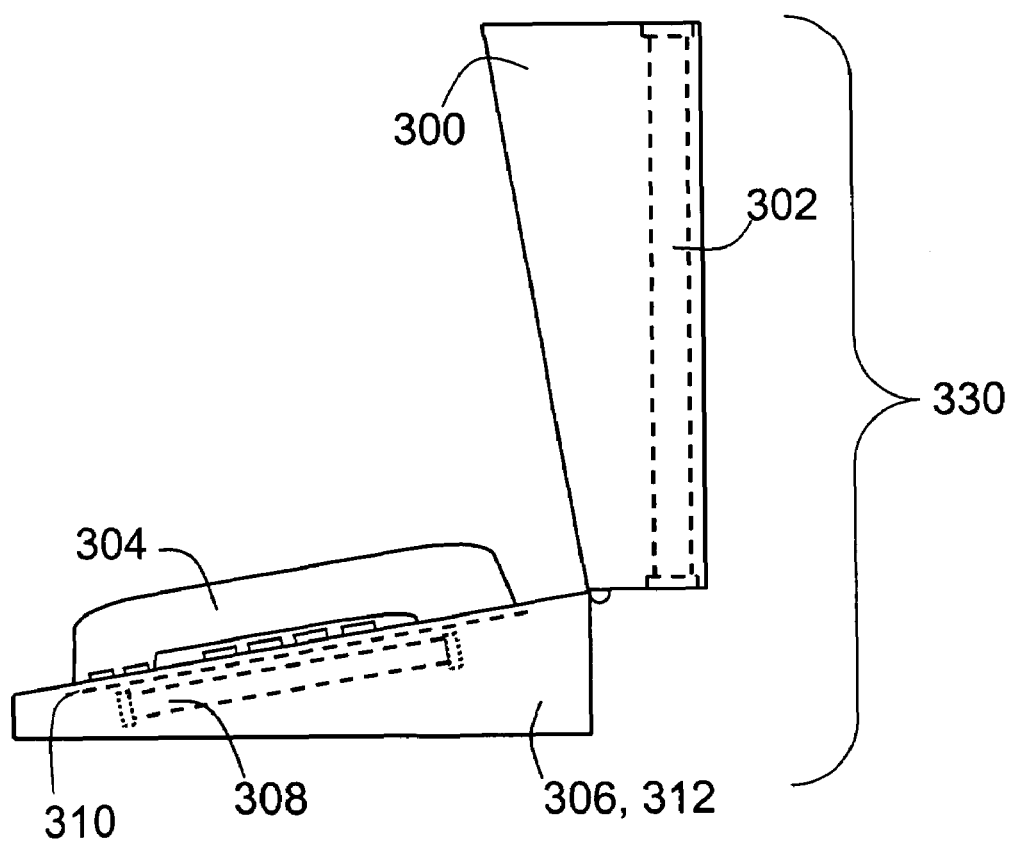
Figure 6B:
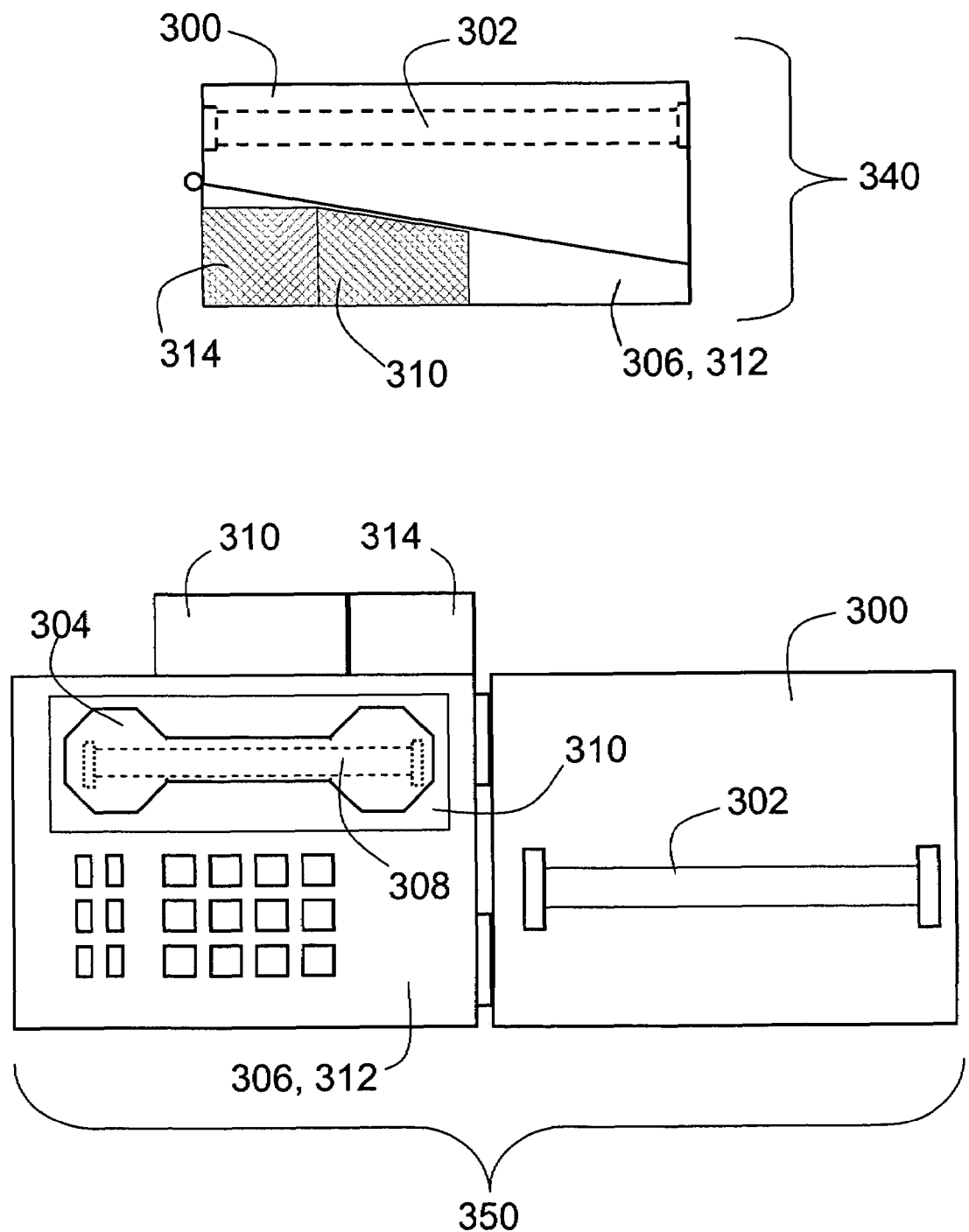
FIG. 6B illustrates a left side view and a top-down view of a UV system for sterilizing a telephone.

FIGS. 6A-B describe a UV system for sterilizing a telephone. FIG. 6A shows right side views of the UV system at open 320 and closed 330 states. The UV system includes a movable closure element 300 attached to a base 306. The base 306 is a housing for enveloping the telephone or other fomites inside the base 306. In the preferred implementation, the telephone is permanently attached to the base 306. In some implementations, the telephone is integrally formed with the base 306. In other implementations, the telephone is detachably attached to the base 306. The movable closure element 300 can be implemented as a cover, a door or other suitably movable element. The closure element 300 also includes an UV light source 302 attached to an interior surface. The closure element 300 is composed of a material or a combination of materials designed to prevent transmission of electromagnetic radiation in the UV range. The closure element 300 can be transparent or translucent, allowing adequate visible light to transmit through the material and allow a user to see through the closure element 300.

The base 306 houses a control unit 312 of a telephone. The control unit 312 includes a numbered keypad and associated electrical components that enable the telephone to function properly. Resting on the control unit 312 is a receiver (handset) 304 used to transmit and receive audio signals. Located underneath the receiver 304 and attached to the control unit 312 is a plate 310 composed of transparent or translucent material designed to transmit electromagnetic radiation in the UV range. For example, the plate 310 can be located at the bottom of a well designed to receive and hold the receiver 304 in place and resting on the control unit 312. Located below the plate 310 is a second UV light source 308. This second UV light source 308 is designed to direct electromagnetic radiation in the UV range towards the underside of the receiver having an earpiece and a mouthpiece.

FIG. 6B represents a left side view 340 and a top-down view 350 the UV system for sterilizing a telephone. Attached to the left side of the base 306 is a automatic controller 310 and a motor 314. The automatic controller 310 is a motion sensor that detects the movement of the user's hand to activate the motor 308 to transition the closure element 300 from a closed state (shown at 320, 340) to an open state (shown at 330, 350). For example, the automatic controller 310 can be a sensor bay, and when the light beam in the sensor bay is interrupted, the motor 314 is triggered to open the closure element 300. In some implementations, the automatic controller 310 can be selected from other suitable motion sensors including a microwave motion sensor, an infrared motion sensor, and an infrared combination motion and presence sensor.

In some implementations, the automatic controller 310 and the motor 314 are implemented to be placed on the right side of the base or other suitable locations.

Operation of the UV system for sterilizing a telephone is similar to the process described in FIG. 5 above with respect to the UV system for sterilizing a computer keyboard 104. When the closure element 300 is closed, both the first UV light 302 and the second UV light 308 are turned on to sterilize the enclosed phone and all internal surfaces of the UV system. As described with respect to FIG. 5 above, the UV light sources 302, 308 can be operated in one of three modes. The UV system can be implemented to allow a user to program and select the desired mode or the UV system can be implemented with a predetermined mode already programmed at the time of manufacture. For implementations allowing the user to select and program the mode, a user interface similar to the programmable timer 114 (FIG. 1A) can be implemented (not shown).

To use the telephone, the user waves his hand or otherwise applies appropriate motion near the automatic controller 310 to activate the sensor bay and engage the motor 308 to open the closure element 300 automatically in a "touch-less" fashion. Although FIG. 6B shows the closure element 300 hinged to the base 306 at a surface near the top of the telephone, the hinge can be implemented at any suitable surfaces. Opening of the closure element 300 automatically shuts off both UV light sources 302, 308 to prevent harmful exposure of the user to UV radiation. When the user has finished using the telephone, the user waves his hand or otherwise applies appropriate motion near the automatic controller 310 to activate the sensor bay and automatically close the closure element 300.

Some optional elements can also be implemented to facilitate the operation of the telephone by the user. For example, a call display unit (not shown) can be attached on the exterior surface of the closure element 300. The call display unit can be implemented to identify the phone line when a call comes in. This can be accomplished with a flashing light representing each phone line. Alternatively, an LED display can be implemented to display and identify the active phone line. In some implementations, other suitable visual display devices can be implemented. The call display unit is especially useful if the closure element 300 is implemented to not allow a user to see into the UV system.

In some implementations, the UV system encloses, either permanently or removably, a cordless or wireless telephone. In such implementations, the UV system is modified to accommodate a difference in overall design of the cordless or wireless telephone as compared to the traditional wired telephone described in FIGS. 6A-B. For example, the second UV light source 308 is not required to be activated whenever the receiver 304 is not resting on the control unit 312. The second UV light source 308 is activated whenever the receiver 308 is charging on the control unit 302.

The UV system for sterilizing a telephone is implemented to allow an existing stand alone telephone to be inserted inside the base 306 and the closure element 300. However, in some implementations, the UV system is manufactured as a self-contained system with a built-in telephone permanently attached.

While, FIGS. 6A-B discloses a UV system enveloping a telephone, the UV system can be modified to envelop other suitable fomites including user interface fomites such as a computer keyboard and a mouse.

Optional Computer Implementation

In some implementations, operation of the UV system as described in FIGS. 1-6 can be implemented to be controlled by one or more computer programs comprising computer executable code stored on a computer readable medium and executing on a computing device. The computing device can be integrated into the automatic controller 110, the electrical interface 112, the programmable timer 114 or a combination of one or more of these elements. Alternatively, an independent computing device can be implemented on an internal or an external surface of the UV system disclosed in FIGS. 1-4 and 6 above. In some implementations, the operation of the UV system can be controlled using a remote control device or an external computing device. The computer readable medium may include a hard disk drive, a flash memory device, a random access memory device such as DRAM and SDRAM, removable storage medium such as CD-ROM and DVD-ROM, a tape, a floppy disk, a CompactFlash memory card, a secure digital (SD) memory card, or some other storage device. In some implementations, the computer executable code may include multiple portions or modules, with each portion designed to perform a specific function described in connection with FIG. 5 above.

In some implementations, the operation of the UV system as disclosed in FIGS. 1-6 can be controlled using hardware such as a microprocessor, a microcontroller, an embedded microcontroller with internal memory, or an erasable programmable read only memory (EPROM) encoding computer executable instructions. For example, the microprocessor can include erasable and modifiable instructions for controlling the motors 103, 308; the closure elements 104, 300; the automatic controllers 110, 310, and the UV light sources 106, 302, 308. The microprocessor can also coordinate the operations of each of the elements of the UV system. In other implementations, the operation of the UV system may be implemented using a combination of software and hardware.

Processors suitable for the execution of a computer program include, by way of example, both general and special purpose microprocessors, and any one or more processors of any kind of digital computer, including graphics processors, such as a GPU. Generally, the processor will receive instructions and data from a read only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of non volatile memory, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

A number of embodiments have been described. Nevertheless, it will be understood that various modifications may be made without departing from the scope of the techniques. For example, the motors 108 and 308 can be substituted with other suitable mechanical or electromechanical devices that impart motion such as a solenoid. In addition, the specific locations of the UV light sources 106, 302 and 308 can be varied to other suitable locations inside the housing 102, the base 306, and the closure elements 104 and 300. Accordingly, other embodiments are within the scope of the following claims.

What is claimed is:

1. An apparatus for sterilizing a fomite, the apparatus comprising:
    a housing configured to envelop a fomite inside the housing, the housing composed of a material configured to prevent transmission of electromagnetic radiation in the ultraviolet range;
    a closure element providing access to inside the housing, the closure element composed of a material configured to transmit electromagnetic radiation in the visual range and prevent transmission of electromagnetic radiation in the ultraviolet range; and
    an ultraviolet light source inside the housing and configured to sterilize the fomite inside the housing by directing ultraviolet electromagnetic radiation towards the fomite.

2. The apparatus of claim 1, wherein the closure element comprises an automated closure element.

3. The apparatus of claim 1, wherein the ultraviolet light source is configured to attach to an internal surface of the closure element.

4. The apparatus of claim 1, wherein the closure element comprises a door.

5. The apparatus of claim 1, wherein the closure element comprises a sliding closure element.

6. The apparatus of claim 1, wherein the closure element comprises a rotating closure element.

7. The apparatus of claim 1, wherein the closure element comprises an integrally formed closure element.

8. The apparatus of claim 1, wherein the closure element comprises two or more separate pieces.

9. The apparatus of claim 1, wherein the fomite is permanently fixed within the housing.

10. The apparatus of claim 1, wherein the fomite is detachably connected to the housing.

11. The apparatus of claim 1, wherein the fomite comprises a computer keyboard.

12. The apparatus of claim 10, wherein the housing is further configured to envelop a computer mouse inside the housing.

13. The apparatus of claim 1, wherein the fomite comprises a telephone, the telephone comprising a receiver and a control module.

14. The apparatus of claim 13, further comprising a second ultraviolet light source configured to sterilize the receiver by directing ultraviolet electromagnetic radiation towards an underside of the receiver.

15. The apparatus of claim 13, further comprising a display unit located on an external surface of the closure element, the display unit configured to provide visual cues to a user and facilitate operation of the telephone.

16. The apparatus of claim 15, wherein the display unit is an LED display.

17. The apparatus of claim 1, further comprising an interface module.

18. The apparatus of claim 17, wherein the interface module comprises a power outlet for plugging-in power cords.

19. The apparatus of claim 17, wherein the interface module comprises a computer input/output interface for providing a physical connection between the fomite located inside the housing and an external computing device.

20. The apparatus of claim 19, wherein the computer input/output interface comprises at least one of a universal serial bus port, a FireWire port, a peripheral component interconnect port, a serial interface port, and a parallel interface port.

21. The apparatus of claim 17, wherein the interface module comprise a telephone jack.

22. The apparatus of claim 1, further comprising an automatic switch communicatively linked to the closure element, wherein the automatic switch is configured to turn-on the ultraviolet light source for a predetermined period of time when the closure element is closed and to automatically turn-off the ultraviolet light source when the closure element is open.

23. The apparatus of claim 1, further comprising a programmable timing module communicatively linked to the automatic switch and the closure element, wherein the programmable timing module is configured to periodically turn-on and turn-off the ultraviolet light for a predetermined period of time.

24. The apparatus of claim 1, further comprising:
a motor communicative linked to the closure element and configured to automatically open and close the closure element; and
an automatic control module communicatively linked to the motor and configured to send a signal to the motor to automatically open and close the closure element.

25. The apparatus of claim 22, wherein the automatic control module comprises a motion detector.

26. A method of sterilizing a fomite, the method comprising:
placing a fomite within a housing, the housing composed of a material configured to prevent transmission of electromagnetic radiation in the ultraviolet range;
closing a closure element movably attached to the housing; and
activating an ultraviolet light source within the housing, the ultraviolet light source communicatively linked to the closure element, wherein the ultraviolet light source is configured to sterilize the fomite by directing ultraviolet radiation towards the fomite for a predetermined period of time when the closure element is closed and to automatically turn-off when the closure element is open.

27. The method of claim 26, wherein the fomite comprises a computer keyboard.

28. The method of claim 26, wherein the fomite comprises a telephone, the telephone comprising a receiver and a control unit.

29. The method of claim 26, wherein the fomite is permanently fixed within the housing.

30. The method of claim 26, wherein the fomite is detachably fixed within the housing.

31. The method of claim 28, further comprising activating a second ultraviolet light source, the second ultraviolet light source configured to sterilize the receiver by directing ultraviolet electromagnetic radiation towards the underside of the receiver.

32. The method of claim 26, wherein closing the closure element comprises activating an automatic control module communicatively linked to a motor and to send a signal to the motor to open and close the closure element.

33. The method of claim 32, wherein the automatic control module comprises a motion detector.

34. The method of claim 26, further comprising providing an interface module on the housing, the interface module comprising a power outlet for plugging-in power cords and a computer input/output interface.

* * * * *